United States Patent [19]

Sakata et al.

[11] Patent Number: 4,634,671

[45] Date of Patent: Jan. 6, 1987

[54] WATER-SOLUBLE CROSS-LINKED POLYMER OF LYSYL ENDOPEPTIDASE, PROCESS FOR PREPARING SAME AND USE OF SAME

[75] Inventors: Yoshitsugu Sakata, Kyoto; Akinori Shintani, Hyogo; Tetsuya Matsuo, Osaka; Haruhiko Sugiyama, Shiga; Nobuyuki Tokioka, Hyogo, all of Japan

[73] Assignee: Wako Pure Chemical Industries, Ltd., Osaka, Japan

[21] Appl. No.: 533,730

[22] Filed: Sep. 19, 1983

[30] Foreign Application Priority Data

Sep. 18, 1982 [JP] Japan ............................ 57-162976

[51] Int. Cl.$^4$ .................. C12N 9/96; C12N 9/50; C12N 9/52; C12P 21/00
[52] U.S. Cl. ............................. 435/188; 435/68; 435/219; 435/220; 435/177
[58] Field of Search ............... 435/177, 188, 220, 179, 435/180, 253; 260/112 R, 121

[56] References Cited

U.S. PATENT DOCUMENTS

| | | | |
|---|---|---|---|
| 3,654,083 | 4/1972 | Moelker | 435/177 |
| 4,256,833 | 3/1981 | Ali et al. | 435/7 |
| 4,266,029 | 5/1981 | Branner-Jorgensen | 435/176 |
| 4,337,313 | 6/1982 | Hershberger et al. | 435/177 |
| 4,411,996 | 10/1983 | Lloyd | 435/94 |
| 4,464,468 | 8/1984 | Avrameas et al. | 435/177 |

FOREIGN PATENT DOCUMENTS 2919622 11/1980 Fed. Rep. of Germany ...... 435/188
0069877 6/1978 Japan ................................ 435/188

OTHER PUBLICATIONS

Martinek et al, Chem. Abst., vol. 92, No. 2421m, 1980, "Role of Intramolecular Cross-Links of Different Length for Maintaining the Catalytically Active Conformation of the Enzyme".
Torchilin et al, Chem. Abst., vol. 91, No. 34911s, 1979, "Principles of Enzyme Stabilization, V. The Possibility of Enzyme Self Stabilization Under the Action of Potentially Reversible Intramolecular Cross-Linkages of Different Length".
Guire, Chem. Abst., vol. 88, No. 33848c, 1977, "Affinity Cross-Linking Agents for Enzyme Stabilization and Immobilization".
Masaki et al, Chem. Abst., vol. 95, No. 92892e, 1981, "Studies on a New Proteolytic Enzyme from *Achromobacter lyticus* M497-1, Specificity and Inhibition Studies of *Achromobacter protease* I".
Klemes et al, Biochim. Biophys. Acta, vol. 567, pp. 401–409, 1979, "Catalytic and Conformational Properties of X-Linked Derivatives of Penicillinase".

Primary Examiner—Thomas G. Wiseman
Assistant Examiner—Robin Lyn Teskin
Attorney, Agent, or Firm—Sughrue, Mion, Zinn, Macpeak, and Seas

[57] ABSTRACT

A water-soluble cross-linked polymer of the enzyme lysyl endopeptidase produced by *Achromobacter lyticus* and a process for preparing the polymer as well as a semi-synthesis of human insulin using the polymer.

22 Claims, 2 Drawing Figures

WATER-SOLUBLE CROSS-LINKED POLYMER OF LYSYL ENDOPEPTIDASE, PROCESS FOR PREPARING SAME AND USE OF SAME

FIELD OF THE INVENTION

The present invention relates to a water-soluble cross-linked polymer of the enzyme lysyl endopeptidase (hereinafter PLP) and a process for preparing the polymer as well as a semi-synthesis of human insulin using the polymer.

BACKGROUND OF THE INVENTION

Enzyme reactions employing PLP are widely known and utilized. However, PLP is generally employed in an aqueous solution containing the substrate. In such a system, the recovery of PLP after completion of the reaction is extremely difficult. In addition, it is difficult to separate and purify the reaction product in such a system. Further, PLP is not a stable enzyme. Thus, when PLP is employed at neutral pH, room temperature and under normal pressure, the recovery of such is markedly lost. It is thus desired that PLP be stable at wide temperature ranges, at wide pH ranges, and in various solvents and can be recovered easily and stably.

PLP is an exo-enzyme produced by *Achromobacter lyticus* M 497-1 separated from soil, found by Soejima and Masaki et al deposited in the Foundation, Institute for Fermentation, Osaka under IFO 12725, American Type Culture Collection under ATCC 21456, and Fermentation Research Institute, Agency of Industrial Science and Technology, Ministry of International Trade and Industry of Japan under FERM-P 4420, and is the same enzyme as Achromobacter protease I described in *Agricultural and Biological Chemistry*, 42:1442 (1978) and Japanese Patent Application (OPI) No. 119085/79.

PLP specifically hydrolyzes the ester bond and the amide bond at the carboxyl group of L-lysine and therefore is useful for semi-synthesis of human insulin from porcine insulin.

It is well known that the optimum temperature of the enzymatic activity of PLP is about 45° C. When casein is used as a substrate, the optimum pH of enzymatic activity is between 8.5 and 10.5. The molecular weight thereof determined by gel filtration is 27,000. The isoelectric point of PLP is pH 6.9. PLP is a serine enzyme that is strongly inhibited by diisopropyl phosphofluoride and tosyl-L-lysine chloromethyl ketone but is not inhibited by tosyl-L-phenylalanine chloromethyl ketone, ethylene-diaminetetraacetate, orthophenanthroline or p-chloromercury benzoate.

The conventional semi-synthesis of human insulin from porcine insulin involves a separation step and requires much time since PLP is used in an aqueous reaction in the form of its monomer and no contamination of human insulin is permitted. In addition, during the separation step, PLP is inactivated in this semi-synthesis and thus it is impossible to reuse the recovered PLP. This is a serious economical drawback in the use of PLP monomers.

Enzyme immobilization has been employed with PLP, however, immobilized PLP becomes insoluble and thus the enzyme reaction must be carried out in a suspension state, etc. Hence, special devices and skill are required for a smooth reaction. That is, a device for effective stirring to obtain a uniform suspension state and a column for prolonging the contact time are necessary. In addition, the use of a relatively large amount of a suitable organic solvent in combination with the use of a large excess of enzyme is disadvantageously required in such a system.

SUMMARY OF THE INVENTION

An object of the present invention is to provide PLP which is stable at various pHs and temperatures and it is soluble in water.

Another object of the present invention is to provide PLP which can be used in an aqueous reaction system and does not have to be immobilized.

A further object of the present invention is to provide PLP which is easily separated and purified from a reaction system.

An additional object of the present invention is to provide a process for producing a water-soluble cross-linked polymer of PLP.

A still further object of the present invention is to provide a process for semi-synthesizing human insulin using PLP.

The above objects have been met by the use of a water-soluble cross-linked polymer of PLP that is obtained by cross-linking PLP intermolecularly or by copolymerization of PLP in the presence of a spacer and/or a water-soluble protein.

BRIEF DESCRIPTION OF THE DRAWINGS

In FIGS. 1 and 2, the curves are defined as follows:
— water-soluble cross-linked polymer of PLP in accordance with the present invention
——— water-soluble cross-linked polymer of PLP in accordance with the present invention
- - - - PLP prior to polymerization

DETAILED DESCRIPTION OF THE INVENTION

Figure 1:
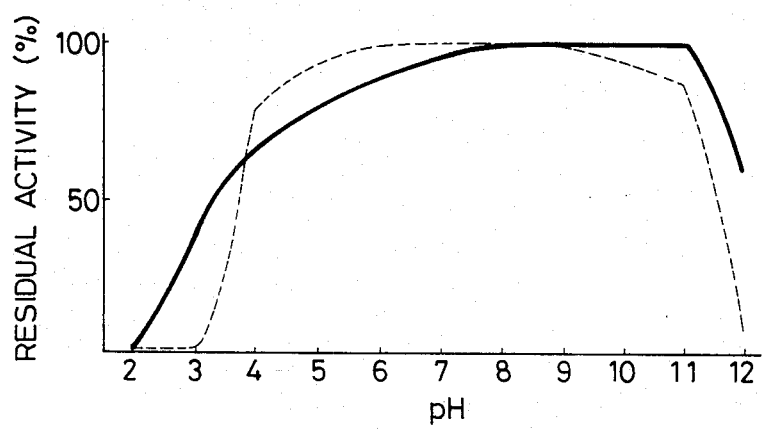
FIG. 1 is a graph showing the pH stability of the cross-linked polymer of PLP of the present invention.

As stated above, the enzyme of the present invention is lysyl endopeptidase produced by *Achromobacter lyticus* (Achromobacter protease I) (see Japanese Patent Application (OPI) No. 119085/79). The water-soluble cross-linked polymer of PLP is obtained by cross-linking PLP intermolecularly, or by copolymerization of PLP in the presence of a spacer and/or a water-soluble protein.

The water-soluble cross-linked PLP polymer of the present invention is a polymer of PLP that has been cross-linked with a polyfunctional organic compound or the like, and if desired in the presence of a polyamine as a spacer and/or a water-soluble protein.

In general, when an enzyme is polymerized in any process, its active site changes and its enzyme activity is decreased. However, the polymer of the present invention shows no decrease in activity when polymerized.

The water-soluble cross-linked PLP polymer of the present invention has a molecular weight of from about 400,000 to about 700,000, and is extremely stable over a wide range of pH and temperature and exhibits enzyme activity equivalent to that of PLP prior to polymerization. Further, the polymer of the present invention can be immobilized to carriers if desired.

In the cross-linking polymerization of PLP, the final concentration of PLP in the reaction liquid is adjusted to generally 0.2 to 20 wt%, preferably 1.0 to 15 wt%.

When the enzyme concentration is lower than 0.2 wt%, the yield of the cross-linked PLP polymer of the present invention is decreased and is not practically useful. When the enzyme concentration is greater than 20 wt%, the product loses its water solubility.

The thus adjusted PLP aqueous solution is used in combination with any one of the cross-linking agents, spacers or water-soluble proteins of the present invention as shown in Table 1.

TABLE 1

| PLP | Cross-Linking Agent | Spacer | Water-Soluble Protein |
|---|---|---|---|
| 0 | 0 | — | — |
| 0 | 0 | 0 | — |
| 0 | 0 | — | 0 |
| 0 | 0 | 0 | 0 |

Examples of the cross-linking agent which can be used in the present invention include: polyaldehydes such as glutaraldehyde, etc.; polyisocyanates such as hexamethylene diisocyanate, toluene diisocyanate, etc. It is preferred that the cross-linking agent be used at a concentration of about 1.0 to 5.0%. When the concentration is greater than 5.0%, the reaction becomes vigorous and insolubilization or the like occurs. When the concentration is less than 1%, the yield is decreased.

Examples of spacers which can be used in the present invention include: polyamines such as spermine, spermidine, etc. The spacers can be used in an amount of from 0.005 to 20 wt%, preferably 0.1 to 1 wt%, and most preferably, 0.02 to 0.01 wt% based on the weight of the reaction liquid.

Examples of water-soluble proteins which can used in the present invention include: proteins such as albumin, water-soluble gelatin and the like. The water-soluble proteins can be used in an amount of from 0.01 to 10 wt%, preferably 0.1 to 5 wt%, and most preferably 0.5 to 3 wt% based on the weight of the reaction liquid.

In preparing the polymer of the present invention, any of the combinations as described in Table 1 is prepared and these mixtures are incubated generally around pH 7.0 at about 30° C. for several minutes to 30 hours to cause cross-linking polymerization.

Thereafter, the raw materials are removed by, for example, dialysis, gel filtration, ultra-filtration, ultra-centrifugation, polyacrylamide gel electrophoresis, or isoelectric point electrophoresis such as ampholine, etc.

The thus obtained cross-linked PLP polymer of the present invention can be used in an enzyme reaction as it is or can be stored in a buffer solution having a suitable pH at 30° C. or lower, or, as a freeze dried product.

The resulting polymer exhibits extremely effective enzyme reaction activity. Further, the polymer can be immobilized in any conventional manner and effectively used as such.

The water-soluble cross-linked PLP polymer in accordance with the present invention shows extremely high activity and specificity. Further, pH stability, heat stability and stability in various media of the PLP of the present invention is markedly high as compared to PLP prior to polymerization.

The stability of the water-soluble cross-linked polymers obtained in Example 1 described below is shown in Tables 2, 3 and 4, in comparison with PLP prior to polymerization.

TABLE 2

Stability in 0.1 M $NH_4HCO_3$ (pH 8.3)
(stored at 37° C. and indicated by a residual activity ratio)

| Storage Time (Hr.) | 42 | 72 | 90 | 138 | 282 |
|---|---|---|---|---|---|
| Cross-linked polymer | 93% | 72% | 69% | 44% | 14% |
| PLP prior to polymerization | 52% | 33% | 29% | 17% | 2% |

TABLE 3

Stability in 0.5 M Tris-Hydrochloride (pH 6.5), Dimethylformamide and Ethanol (7 volume:5 volume:5 volume)
(stored at 37° C. and indicated by a residual activity ration)

| Storage Time (Hr.) | 24 | 42 | 90 | 234 |
|---|---|---|---|---|
| Cross-linked polymer | 95% | 92% | 73% | 46% |
| PLP prior to polymerization | 86% | 82% | 65% | 33% |

TABLE 4

Stability in 0.5 M Acetic Acid (pH 2.5)
(stored at 4° C. and indicated by a residual activity ratio)

| Storage Time (Hr.) | 4 | 48 | 78 | 96 | 144 | 288 |
|---|---|---|---|---|---|---|
| Cross-linked polymer | 67% | 51% | 43% | 41% | 34% | 26% |
| PLP prior to polymerization | 55% | 40% | 27% | 16% | 10% | 3% |

In Tables 2, 3 and 4 above, the activities of the enzymes were measured as follows: To 2.6 ml of a 0.2 mol/liter 2-amino-2-methyl-1,3-propanediol buffer solution (pH 9.5), 0.3 ml of a 2.5 mM aqueous benzoyllysine-p-nitroanilide solution was added. After pre-warming at 30° C., 0.1 ml of the enzyme was added to the mixture and the mixture was reacted for 25 minutes at 30° C. After completion of the reaction, 1.0 ml of a 45% acetic acid aqueous solution was added to discontinue the reaction. Then, the reaction liquid was colorimetrically measured at 405 nm to determine absorbence.

The amount of enzyme producing 1 micromole/min of p-nitroaniline at 30° C.=1 unit (u). Enzyme activity was calculated according to the following equation:

Activity (u/ml) =

$$\frac{\Delta OD}{min} \times \frac{1}{9.62} \times \frac{4.0}{0.1} \times \text{dilution magnification}$$

The activity of the PLP of the present invention on various substrates is shown in Table 5 below. These reactions were carried out in the following manner:

A liquid mixture of 0.1 ml of 0.144 units of the cross-linked polymer of the present invention, 0.3 ml of a 2.5 mM solution of each of the substrates described in Table 5 and 2.6 ml of a 0.2M 2-amino-2-methyl-1,3-propanediol buffer solution (pH 9.5) were reacted at 30° C. Thereafter, activities on the respective substrates were measured according to the method for measuring activity described above.

TABLE 5

| | Relative Activity (%) | |
|---|---|---|
| Substrate | Cross-linked Polymer | PLP prior to Polymerization |
| Benzoyl lysine-p-nitro anilide | 100 | 100 |

TABLE 5-continued

| Substrate | Relative Activity (%) | |
|---|---|---|
| | Cross-linked Polymer | PLP prior to Polymerization |
| Lysine-p-nitroanilide | 5.6 | 2.4 |
| Benzoyl arginine-p-nitroanilide | 0.04 | 0.01 |
| Leucine-p-nitroanilide | 0.00 | 0.00 |
| Alanine-p-nitroanilide | 0.00 | 0.00 |
| Glutamic acid-p-nitroanilide | 0.00 | 0.00 |
| Benzoyl tyrosine-p-nitroanilide | 0.00 | 0.00 |
| Acetylphenylalanine-p-nitroanilide | 0.00 | 0.00 |

As is evident from Table 5, above, the water-soluble cross-linked PLP polymer of the present invention strongly acts on the carboxyl group bonds of lysine but poorly acts on the carboxyl group bonds of arginine. Further, the PLP of the present invention does not hydrolyze the carboxyl group bonds of other amino acids.

When using the cross-linked PLP polymer of the present invention, the polymer is mixed with its substrate; after reacting the mixture under optimum conditions, the cross-linked PLP polymer of the present invention can be recovered by gel filtration or ion exchange materials, etc. Such an easy separation and recovery is one of the advantages of the present invention. At the same time, the cross-linked PLP polymer of the present invention can be repeatedly used because there is no loss in its enzyme activity.

Due to the specific activity and stability of the polymer, the polymer can be utilized for enzyme decomposition of peptides in the determination of amino acid configuration, decomposition and synthesis of lysyl peptides, e.g., semi-synthetic human insulin, etc.

Known methods for converting porcine insulin into human insulin include chemical methods as described in Lettenberg, Science, 177:623 (1972); Geiger, et al., Physiological Chemistry, 357:759 (1976) and enzyme methods as described in Japanese Patent Application (OPI) No. 18799/80, etc. The chemical methods are disadvantageous since they are complicated, produce many by-products and provide low yields.

Due to the water solubility of the cross-linked PLP polymer of the present invention, the reaction for producing semi-synthetic human insulin can be performed in a homogeneous system. Further, due to the high stability of the cross-linked PLP polymer of the present invention, it is possible to recover and repeatedly use the polymer without losing its enzyme activity. In addition, the enzyme reaction can be carried out in high yield in water alone or in the system in which organic solvents miscible with water are used in combination. Further, due to the high molecular weight of the cross-linked PLP polymer of the present invention, separation and purification of the product as well as recovery of the cross-linked PLP polymer of the present invention are extremely advantageous since the product can easily be taken out by, for example, molecular sieve gel filtration.

Utilization of the cross-linked polymer of the present invention for semi-synthesis of human insulin can occur in, for example, the following two reactions. One reaction comprises reacting porcine insulin, L-threonine in which the carboxyl group is protected or unprotected (hereinafter represented by Thr-OR, wherein R is hydrogen or substituted or unsubstituted alkyl or aralkyl) and the cross-linked PLP polymer in accordance with the present invention. In this manner, PLP can be used to prepare a human insulin derivative having Thr-OR at $B_{30}$. Then, the derivative can be converted into human insulin in a conventional manner.

The second reaction comprises incubating porcine insulin and the cross-linked PLP polymer of the present invention together, digesting $B_{30}$ from the resulting desalanine insulin (hereinafter referred to as DAI), then incubating DAI, Thr-OR and the cross-linked polymer of the present invention to prepare a human insulin derivative having Thr-OR at $B_{30}$ (hereinafter referred to as $B_{30}$RO-Thr-I), and then converting the derivative into human insulin in a conventional manner.

Water alone or one or more organic solvents miscible with water for increasing the solubility of the raw materials can be used with water as reaction solvents.

There is no particular limit to the amount of the organic solvents used. Examples of the organic solvents employed in the present invention include: methanol, ethanol, isopropanol, ethylene glycol, methyl cellosolve, acetone, dioxane, dimethylformamide, dimethyl sulfoxide, etc.

The stability of the water-soluble cross-linked PLP polymer in accordance with the present invention in the above solvents in comparison with PLP prior to polymerization is shown in Table 6 below.

TABLE 6

Stability in a Solvent
(stored at 30° C. in a solvent and indicated by a residual activity ratio)

| Solvent (A 50% aqueous solution) | After 1 hour | | After 24 hours | | After 48 hours | | After 192 hours | |
|---|---|---|---|---|---|---|---|---|
| | A | B | A | B | A | B | A | B |
| Methanol | 105 | 110 | 103 | 113 | 103 | 113 | 105 | 103 |
| Ethanol | 110 | 100 | 107 | 114 | 105 | 112 | 106 | 101 |
| Isopropanol | 104 | 99 | 107 | 114 | 99 | 110 | 103 | 101 |
| Ethylene glycol | 105 | 100 | 110 | 113 | 109 | 115 | 106 | 101 |
| Acetone | 116 | 114 | 120 | 120 | 112 | 122 | 130 | 126 |
| Dimethylformamide | 99 | 104 | 100 | 110 | 99 | 115 | 105 | 97 |
| Dimethyl sulfoxide | 97 | 98 | 92 | 93 | 94 | 97 | 96 | 92 |
| Water | 100 | 112 | 98 | 110 | 92 | 106 | 95 | 88 |

A: cross-linked polymer of the present invention (obtained in Example 1)
B: PLP prior to polymerization Examples of R in Thr-OR include hydrogen, methyl, ethyl, isopropyl, t-butyl, benzyl, etc. The reaction temperature employed is less than 50° C., preferably from 20° to 40° C. The pH employed is from 4 to 10, preferably from 5 to 8. It is desired that the molar concentration ratio of Thr-OR to porcine insulin or DAI be large, i.e., about 1:5 to 1:1000.

As buffering agents of the reaction solution, trishydroxymethylaminomethane, citrate, phosphate buffer solutions, etc. are employed.

It is preferred that the concentration of the cross-linked PLP polymer of the present invention in the reaction solution be about from 0.1 to 10 mg/ml. The reaction time is generally from 3 to 72 hours, preferably in 6 to 24 hours.

The obtained $B_{30}RO$-Thr-I is converted into human insulin in a conventional manner ordinarily used for peptide synthesis, for example, when R is t-butyl, i.e., $B_{30}Bu^tO$-Thr-I, t-butyl is removed by treatment with anisole-trifluoroacetic acid. When R is Thr-OR is hydrogen, i.e., it has been confirmed by using labeled threonine that the reaction of peptide exchange proceeds, but it is not easy to separate and purify the product from raw porcine insulin and such is not preferable.

Human insulin semi-synthesized by the process of the present invention can be converted into medical preparations in a conventional manner and administered to patients, for example, as drugs for treating diabetes.

The following examples are shown for illustrative purpose and are not meant to limit the scope of the present invention in any manner.

In the examples below showing cross-linking polymerization, the yields are shown in a one time polymerization. However, the PLP which was not consumed in the polymerization can again be subjected to subsequent cross-linking polymerization without being damaged.

EXAMPLE 1

Figure 2:
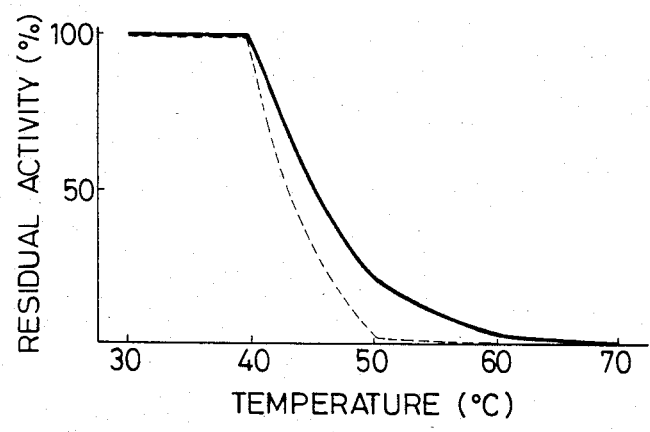
FIG. 2 is a graph showing the heat stability of the cross-linked polymer of PLP of the present invention.

After reacting 10 mg (specific activity, 3.6 u/mg) of PLP and 1.0 ml of a 0.01M phosphate buffer solution (pH 7.2) containing 12.0 mg of glutaraldehyde at 4° C. for 20 hours with stirring, the reaction solution was subjected to gel filtration using a column ($\phi 1.5 \times 87$ cm) of Sephadex G-100 to obtain 17.3 units (specific activity (u/OD$_{230}$) 1.37) of a water-soluble cross-linked PLP polymer in a yield of 48% at about 0.3 in a column volume ratio. Various properties of the product are as follows:

(i) Molecular Weight
  about 450,000 (determined by gel filtration using Sephadex G-200)
(ii) Stability to pH
  Activity was measured after maintaining at 30° C. for 1 hour using a Briton-Robinson buffer solution (pH 2 to 12) as the buffer solution. The results obtained are shown in FIG. 1. From the results in FIG. 1, it can be seen that the enzyme is stable at a pH of 7 to 11.5 and that the optimum pH is about 9.5.
(iii) Stability to Heat
  The product was maintained for 1 hour at various temperatures using a 0.2M 2-amino-2-methyl-1,3-propanediol buffer solution (pH 9.5). The enzyme was stable up to 40° C. as shown in FIG. 2 and the optimum temperature is about 40° C.

EXAMPLE 2

5.0 mg (specific activity 3.8 u/mg) of PLP and 0.2 mg of spermine were added to 0.5 ml of a 0.01M phosphate buffer solution (pH 7.2) containing 6 mg of glutaraldehyde and were reacted at 4° C. for 20 hours. Subsequently, in a manner similar to Example 1, 8.36 units (specific activity (u/OD$_{230}$) 0.797) of water-soluble cross-linked PLP polymer was obtained in a yield of 44%.

Various properties of the resulting product determined according to the measurement methods as in Example 1 are as follows:
(i) Molecular Weight
  about 500,000
(ii) Stability to pH
  Stable at pH of 7 to 11.5
(iii) Stability to Heat
  Stable up to 42° C.

EXAMPLE 3

5.0 mg (specific activity 3.8 u/mg) of PLP and 4.0 mg of water-soluble gelatin (manufacture by Tanabe Pharmaceutical Co., Ltd., NP-2000) were added to 0.2 ml of a 0.01M phosphate buffer solution (pH 7.2). Next, 0.3 ml of the same buffer solution containing 6 mg of glutaraldehyde was added to the solution and the mixture was reacted at 25° C. for 50 minutes. Subsequently, in a manner similar to Example 1, 5.89 units (specific activity (u/OD$_{230}$) 0.702) of a water-soluble cross-linked PLP polymer was obtained in a yield of 31%.

The various properties of the resulting product determined according to the measurement methods described above are as follows:
(i) Molecular Weight
  about 600,000 (this value was determined by gel filtration using Sepharose 6B).
(ii) Stability to pH
  Stable at pH of 6 to 11.
(iii) Stability to Heat
  Stable up to 40° C.

EXAMPLE 4

In 0.2 ml of a 0.01M phosphate buffer solution (pH 7.2), 5.0 mg (specific activity 2.09 u/mg) of PLP, 11.6 mg of bovine albumin and 0.1 mg of spermine were dissolved. After adding 0.3 ml of the same buffer solution containing 6.0 mg of glutaraldehyde to the solution, the mixture was reacted at 4° C. for 4 hours with stirring. Thereafter, in a manner similar to Example 1, 4.50 units (specific activity (u/OD$_{230}$) 0.18) of a water soluble cross-linked PLP polymer were obtained in a yield of 43%.

The molecular weight of the resulting product was measured as in Example 2 and the stability to heat and pH were measured as in Example 1.
(i) Molecular Weight
  about 650,000
(ii) Stability to pH
  Stable at pH of 4 to 11.5
(iii) Stability to Heat
  Stable up to 42° C.

EXAMPLE 5

In 0.35 ml of a 0.01M phosphate buffer solution (pH 7.2), 5.0 mg (specific activity 3.8 u/mg) of PLP was dissolved and 0.05 ml of an acetone solution containing 2.0 mg of hexamethylene diisocyanate and 0.1 ml of a 0.01M phosphate buffer solution (pH 7.2) containing 0.2 mg of spermine were added to the solution. After reacting the mixture at room temperature for 1 hour with stirring, the procedures were performed in the same manner as in Example 1 to obtain 2.8 units (specific activity (u/OD$_{230}$) 0.737) of a water soluble cross-linked PLP polymer in a yield of 14.7%.

The various properties of the resulting product were measured as in Example 1 and are as follows:
(i) Molecular Weight about 450,000 to 500,000
(ii) Stability to pH
  Stable at pH of 7 to 11.0
(iii) Stability to Heat
  Stable up to 42° C.

EXAMPLE 6

0.5 g (wet weight), of Sepharose 4B (manufactured by Pharmacia Co.), activated with cyanogen bromide in a conventional manner and 5.58 units of the water soluble cross-linked PLP polymer obtained in Example 1 were reacted in 2.0 ml of a 0.025M sodium borate buffer solution (pH 8.5) at 4° C. for 20 hours. The solid matter taken out by filtration was washed sequentially with a 0.025M sodium borate buffer solution (pH 8.5); the same buffer solution (pH 8.5) containing 1.0M sodium chloride; a 0.1M sodium acetate buffer solution (pH 5.0) containing 1.0M sodium chloride; a 0.1M sodium hydrogen carbonate aqueous solution containing 1.5% glycine; and a 0.01M tris-hydrochloride buffer solution (pH 8) in order to obtain 0.5 g (wet weight) of immobilized enzyme of the cross-linked PLP polymer (activity 0.862 unit/0.5 wet carrier).

EXAMPLE 7

To 2 ml of a 0.01M phosphate buffer solution (pH 5.5) containing 5.34 units of the water-soluble cross-linked PLP polymer obtained in Example 1, 1.0 g (wet weight) of Amberlite CG-50 (made by Rohm Haas Co.) which had previously been activated was added to form a suspension. While stirring the suspension at 4° C., 2.0 ml of the same buffer solution containing 100 mg of 1-ethyl-3-[3-(dimethylamino)propyl]-carbodiimide hydrochloride was gradually added to the suspension at 4° C. The mixture was reacted at the same time for an additional 15 hours. The solid matter taken out by gel filtration was washed sequentially with the same buffer solution; the same buffer solution containing 1.0M sodium chloride; and a 2.0 mM tris-hydrochloride buffer solution (pH 8.0) in order to obtain 1.0 g (wet weight) of immobilized enzyme of the cross-linked PLP polymer (activity 0.66 unit/1.0 g wet carrier).

EXAMPLE 8

To 100 mg (concentration 2 mM) of porcine insulin and 3.08 g (concentration 2M) of Thr-OBu$^t$ (R=tertiary butyl in Thr-OR) neutralized with 3.5 ml of 5M acetic acid, a 2.0M acetate buffer solution (pH 5.5) containing 40% of a mixture of ethanol-dimethylformamide (1 vol:1 vol) was added to dissolve and make the total volume 8.5 ml. Next, 0.3 ml of a condensed liquid of the water-soluble cross-linked PLP polymer obtained in Example 1 having 10 amidase activity units/ml liquid was added and the mixture was maintained at 37° C. overnight. By confirmation with high speed liquid chromatography, $B_{30}Bu^tO$-Thr-I was formed in a yield of 65%.

Next, the reaction solution mixture was passed through a column ($\phi 4 \times 200$ cm) of ultra-fine Sephadex G100 and subjected to gel filtration with a 0.5M acetate buffer solution (pH 5.0) to fractionate into an enzyme fraction, an insulin fraction and a Thr-OBu$^t$ fraction.

The enzyme and substrate fractions could then be reused by condensing the enzyme fraction or by freeze-drying the enzyme fraction followed by pulverizing, or by freeze drying the Thr-OBu$^t$ fraction. The activity recovery rate of the enzyme fraction, i.e., the water-soluble PLP cross-linked polymer, was 95%.

After freeze drying, the insulin fraction was passed through a column ($\phi 2 \times 25$ cm) of DEAE Sephadex A25 equilibrated with a 7.0M urea solution. Next, 800 ml of the elution buffer solution described above at 4° C., wherein the concentration of sodium chloride in the elution was linearly graduated up to 0.3M, was added to the column so as to fractionate out the 0.08–0.13M fraction and the 0.17–0.21M fraction. After immediately dialyzing both fractions against a 0.01M ammonium acetate solution in the cold for 3 to 4 days, freeze drying was immediately performed. From the former fraction, 55 mg of $B_{30}Bu^tO$-Thr-I powder was obtained. The yield was 55%.

To 50 mg of the resulting powder, 2.0 ml of trifluoroacetic acid containing 0.2 ml of anisole was added. After maintaining the mixture at room temperature for 30 minutes, trifluoroacetic acid was removed in a nitrogen flow and 2.0 ml of 1.0M acetic acid was added. Thereafter, anisole was extracted with 15 ml of ether. The acetic acid portion was freeze dried to obtain 43 mg of human insulin.

The product was identified against a standard specimen by slab gel electrophoresis and high speed liquid chromatography and confirmed to be human insulin. At the same time, the product was hydrolyzed with 6.0N hydrochloric acid for 24 hours at 110° C. The product was confirmed to be identical, by amino acid analysis, with the calculated values as described below.

| Amino Acid | Found | Calculated |
| --- | --- | --- |
| Lys | 1.00 | 1 |
| His | 1.83 | 2 |
| Arg | 1.01 | 1 |
| Asp | 3.05 | 3 |
| Thr | 2.76 | 3 |
| Ser | 2.81 | 3 |
| Glu | 7.13 | 7 |
| Pro | 1.11 | 1 |
| Gly | 4.01 | 4 |
| Ala | 1.07 | 1 |
| Val | 3.53 | 4 |
| Ile | 1.48 | 2 |
| Leu | 5.95 | 6 |
| Tyr | 3.77 | 4 |
| Phe | 3.02 | 3 |

EXAMPLE 9

In 40 ml of 0.1M ammonium hydrogen carbonate (pH 8.3), 200 mg of porcine insulin (concentration 0.87 mM) was dissolved and 4.0 mg of the water-soluble cross-linked PLP polymer obtained in Example 1 were added. The mixture was reacted at 37° C. for 24 hours. The amount of alanine formed was quantitatively determined by conventional amino acid oxidase and nihydrin methods to obtain conversion rates of porcine insulin to DAI of 98% and 92%.

The freeze dried reaction solution mixture and 6.2 g (concentration 2.0M) of Thr-OBu$^t$ neutralized with 7.0 ml of 5.0M acetic acid were dissolved in 10 ml of a 0.5M tris buffer solution (pH 6.5) containing 40% of a mixture of ethanol-dimethylformaide (1 vol:1 vol). The resulting solution was kept overnight at 37° C. The formation rate of $B_{30}Bu^tO$-Thr-I, measured by high speed liquid chromatography, was 75%. In a manner similar to Example 7, gel filtration ion exchange chromatography was performed to obtain 120 mg of $B_{30}Bu^tO$-Thr-I. The activity recovery ratio of the water-soluble cross-linked PLP polymer was 92%.

The thus obtained $B_{30}Bu^tO$-Thr-I was identified by high speed liquid chromatography and polyacrylamide gel electrophoresis.

EXAMPLE 10

In 5.0 ml of a 2.0M acetate buffer solution (pH 5.1), 3.1 g (concentration 2.0M) of Thr-OBu$^t$ neutralized with 3.5 ml of 5.0M acetic acid and 100 mg (concentration 2.0 mM) of porcine insulin were dissolved. Next, 0.3 ml of 10 units/ml amidase activity of a condensed liquid of the water-soluble cross-linked PLP polymer obtained in Example 1 was added to the solution and the mixture was kept at 37° C. overnight. The formation rate of $B_{30}Bu^tO$-Thr-I, measured by high speed liquid chromatography, was 60%.

Purification was carried out in a manner similar to Example 8 to obtain $B_{30}Bu^tO$-Thr-I in a yield of 50 mg. The activity recovery ratio of the water-soluble cross-linked PLP polymer was 89%.

EXAMPLE 11

Porcine insulin, 100 mg (concentration 2.0 mM) in 5.0 ml of a 2.0M acetate buffer (pH 5.1) solution and 3.1 g of Thr-OBu$^t$ neutralized with 3.5 ml of 5.0M acetic acid were dissolved by adding 40% of a mixture of methanol-dimethyl sulfoxide (1 vol:1 vol). The total volume made was 8.5 ml. Next, 2.0 mg of the water-soluble cross-linked PLP polymer obtained in Example 2 was added and the mixture was kept at 37° C. overnight. The reaction rate was 60%. In a manner similar to Example 8, $B_{30}Bu^tO$-Thr-I was obtained in a yield of 50 mg and the activity recovery ratio of the water-soluble cross-linked PLP polymer was 93%.

EXAMPLE 12

0.3 ml of 15 amidase activity units/ml of a condensed liquid of the water-soluble cross-linked PLP polymer obtained in Example 3, 100 mg (concentration 2.0 mM) of DAI obtained in Example 9 and 3.1 g (concentration 2.0M) of Thr-OBu$^t$ neutralized with 3.5 ml of 5M acetic acid were dissolved in 5 ml of a 0.5M tris buffer solution containing 40% of a mixture of ethanol-dimethylformamide (1 vol:1 vol) and the resulting solution was kept at 37° C. overnight. The reactivity was 68%. In a manner similar to Example 8, $B_{30}Bu^tO$-Thr-I was obtained in a yield of 55 mg and the activity recovery ratio of the water-soluble cross-linked PLP polymer was 88%.

EXAMPLE 13

4.5 units of the immobilized cross-linked PLP polymer obtained by the procedure of Example 6, 100 mg (concentration 2.0 mM) of the intermediate DAI obtained by the procedure of Example 9 and 3.1 g (concentration 2.0M) of Thr-OBu$^t$ neutralized with 3.5 ml of 5.0M acetic acid were mixed with 5.0 ml of a 2.0M sodium acetate buffer solution (pH 7.0) containing 17% of a mixture of ethanol and dimethylformamide (1 vol:1 vol). The resulting solution was kept at 37° C. with stirring overnight. After filtration, the $B_{30}Bu^tO$-Thr-I was obtained. The formation rate thereof, measured by high speed liquid chromatography, was 65%. The activity recovery ratio of the immobilized cross-linked PLP polymer was 85%.

While the invention has been described in detail and with reference to specific embodiments thereof, it will be apparent to one skilled in the art that various changes and modifications can be made therein without departing from the spirit and scope thereof.

We claim:

1. A water-soluble, intermolecularly cross-linked polymer of Achromobacter protease I having a molecular weight of between 400,000 to 700,000 prepared by the process comprising polymerizing, in solution, about 0.2 to about 20 wt% of Achromobacter protease I derived from *Achromobacter lyticus* with about 1 to about 5 wt% of a polyaldehyde or a polyisocyanate cross-linking agent, at about pH 7.0 at about 30° C. for several minutes to 30 hours.

2. The water-soluble polymer as claimed in claim 1, wherein polymerization is further carried out in the presence of from about 0.01 to about 10 wt% of a water-soluble protein.

3. The water-soluble polymer as claimed in claim 1, wherein polymerization is further carried out in the presence of from about 0.005 to about 20 wt% of a polyamine spacer.

4. The water-soluble polymer as claimed in claim 1, wherein polymerization is further carried out in the presence of from about 0.1 to about 10 wt% of a water-soluble protein and from about 0.005 to about 20 wt% of a polyamine spacer.

5. The water-soluble polymer as claimed in claim 2, wherein said polyaldehyde is glutaraldehyde and said polyisocyanate is selected from the group consisting of hexamethylene diisocyanate and toluene diisocyanate.

6. The water-soluble polymer as claimed in claim 3, wherein said polyamine is selected from the group consisting of spermine and spermidine.

7. The water-soluble polymer as claimed in claim 4, wherein said polyamine is selected from the group consisting of spermine and spermidine.

8. The water-soluble polymer as claimed in claim 1, wherein said *Achromobacter lyticus* has the identifying characteristics of ATCC No. 21456.

9. A process for preparing a water-soluble, intermolecularly cross-linked polymer of Achromobacter protease I having a molecular weight of between 400,000 to 700,000 comprising polymerizing, in solution, about 0.2 to about 20 wt% of Achromobacter protease I derived from *Achromobacter lyticus* with about 1 to about 5 wt% of a polyaldehyde or a polyisocyanate cross-linking agent, at about pH 7.0 at about 30° C. for several minutes to 30 hours.

10. The process for preparing a water-soluble polymer as claimed in claim 9, wherein said polyaldehyde is glutaraldehyde and said polyisocyanate is selected from the group consisting of hexamethylene diisocyanate and toluene diisocyanate.

11. The process for preparing a water-soluble polymer as claimed in claim 9, wherein said *Achromobacter lyticus* has the identifying characteristics of ATCC No. 21456.

12. A process for preparing a water-soluble, intermolecularly cross-linked polymer of Achromobacter protease I having a molecular weight of between 400,000 to 700,000 comprising polymerizing, in solution, about 0.2 to about 20 wt% of Achromobacter protease I derived from *Achromobacter lyticus* with about 1 to about 5 wt% of a polyaldehyde or a polyisocyanate cross-linking agent and about 0.01 to about 10 wt% of a water-soluble protein, at about pH 7.0 at about 30° C. for several minutes to 30 hours.

13. The process for preparing a water-soluble polymer as claimed in claim 12, wherein said polyaldehyde is glutaraldehyde and said polyisocyanate is selected from the group consisting of hexamethylene diisocyanate and toluene diisocyanate.

14. The process for preparing a water-soluble polymer as claimed in claim 12, wherein said *Achromobacter lyticus* has the identifying characteristics of ATCC No. 21456.

15. A process for preparing a water-soluble, intermolecularly cross-linked polymer of Achromobacter protease I having a molecular weight of between 400,000 to 700,000 comprising polymerizing, in solution, about 0.2 to about 20 wt% of Achromobacter protease I derived from *Achromobacter lyticus* with about 1 to about 5 wt% of a polyaldehyde or a polyisocyanate cross-linking agent and about 0.005 to about 20 wt% of a polyamine spacer, at about pH 7.0 at about 30° C. for several minutes to 30 hours.

16. The process for preparing a water-soluble polymer as claimed in claim 15, wherein said polyaldehyde is glutaraldehyde and said polyisocyanate is selected from the group consisting of hexamethylene diisocyanate and toluene diisocyanate.

17. The process for preparing a water-soluble polymer as claimed in claim 15, wherein said polyamine is selected from the group consisting of spermine and spermidine.

18. The process for preparing a water-soluble polymer as claimed in claim 15, wherein said *Achromobacter lyticus* has the identifying characteristics of ATCC No. 21456.

19. A process for preparing a water-soluble, intermolecularly cross-linked polymer of Achromobacter protease I having a molecular weight of between 400,000 to 700,000 comprising polymerizing, in solution, about 0.2 to about 20 wt% of Achromobacter protease I derived from *Achromobacter lyticus* with about 1 to about 5 wt% of a polyaldehyde or a polyisocyanate cross-linking agent, about 0.01 to about 10 wt% of a water-soluble protein and about 0.005 to about 20 wt% of a polyamine spacer, at about pH 7.0 at about 30° C. for several minutes to 30 hours.

20. The process for preparing a water-soluble polymer as claimed in claim 19, wherein said polyaldehyde is glutaraldehyde and said polyisocyanate is selected from the group consisting of hexamethylene diisocyanate and toluene diisocyanate.

21. The process for preparing a water-soluble polymer as claimed in claim 19, wherein said polyamine is selected from the group consisting of spermine and spermidine.

22. The process for preparing a water-soluble polymer as claimed in claim 19, wherein said *Achromobacter lyticus* has the identifying characteristics of ATCC No. 21456.

* * * * *